United States Patent [19]

Duffy

[11] Patent Number: 4,719,061
[45] Date of Patent: Jan. 12, 1988

[54] SYSTEM AND METHOD FOR IN-PROCESS DETECTION OF CONTAMINATION IN ELECTRICAL CONDUCTOR INSULATION

[75] Inventor: Edward K. Duffy, West Lafayette, Ind.

[73] Assignee: Essex Group, Inc., Fort Wayne, Ind.

[21] Appl. No.: 764,811

[22] Filed: Aug. 12, 1985

[51] Int. Cl.⁴ .................................... B29C 47/92
[52] U.S. Cl. ........................... 264/40.2; 264/174; 425/113; 425/135; 425/169
[58] Field of Search ............... 264/40.2, 40.1, 174; 425/135, 140, 141, 174.4, 113, 146, 169–173

[56] References Cited

U.S. PATENT DOCUMENTS

| | | | |
|---|---|---|---|
| 3,278,988 | 10/1966 | Hannis | 264/40.7 |
| 3,710,241 | 1/1973 | Dineen | 425/135 |
| 3,781,531 | 12/1973 | Baker | 235/151.3 |
| 3,898,469 | 8/1975 | Nichols et al. | 250/563 |
| 3,900,265 | 8/1975 | Merlen et al. | 356/200 |
| 3,980,891 | 9/1976 | Slaker | 250/563 |
| 4,197,457 | 4/1980 | Cheo | 250/339 |
| 4,208,126 | 6/1980 | Cheo et al. | 356/51 |
| 4,213,747 | 7/1980 | Friedrich | 425/146 |
| 4,247,204 | 1/1981 | Merlen et al. | 356/431 |
| 4,260,899 | 4/1981 | Baker | 250/563 |
| 4,265,545 | 5/1981 | Slaker | 356/431 |
| 4,289,964 | 9/1981 | Baker | 250/308 |
| 4,363,966 | 12/1982 | Cheo | 250/339 |
| 4,386,707 | 6/1983 | Stube | 209/546 |
| 4,401,893 | 8/1983 | Dehuysser | 250/572 |
| 4,441,124 | 4/1984 | Heebner et al. | 358/106 |

FOREIGN PATENT DOCUMENTS

| | | | |
|---|---|---|---|
| 3306476 | 8/1984 | Fed. Rep. of Germany | 264/40.1 |
| 53-40062 | 4/1978 | Japan | 264/40.2 |
| 59-76225 | 5/1984 | Japan | 264/40.1 |

OTHER PUBLICATIONS

EPRI Information Sheet–Contaminated Polyethylene–Pellet Detector–Mar. 1979.
Contamination Detector for Extrudable Dielectrics, prepared by Reynolds Metal Company–Jul. 1979.
Extra-Clean Crosslinkable Polyethylenes for Medium-& High-Voltage Power Cables, by Union Carbide Corporation–1981.
Laser Inspection of Coated Coils... A New Approach in Quality Management, by Dr. Beverly Politzer–Sept. 30, 1981.

Primary Examiner—Jeffery Thurlow
Attorney, Agent, or Firm—Alan C. Cohen

[57] ABSTRACT

The present invention discloses a method for determining the level of contamination in electrical cable insulation. This is achieved by extruding the cable insulation about the conductor and simultaneously producing a thin ribbon of the insulation which is then screened via a laser beam for contaminants.

3 Claims, 1 Drawing Figure

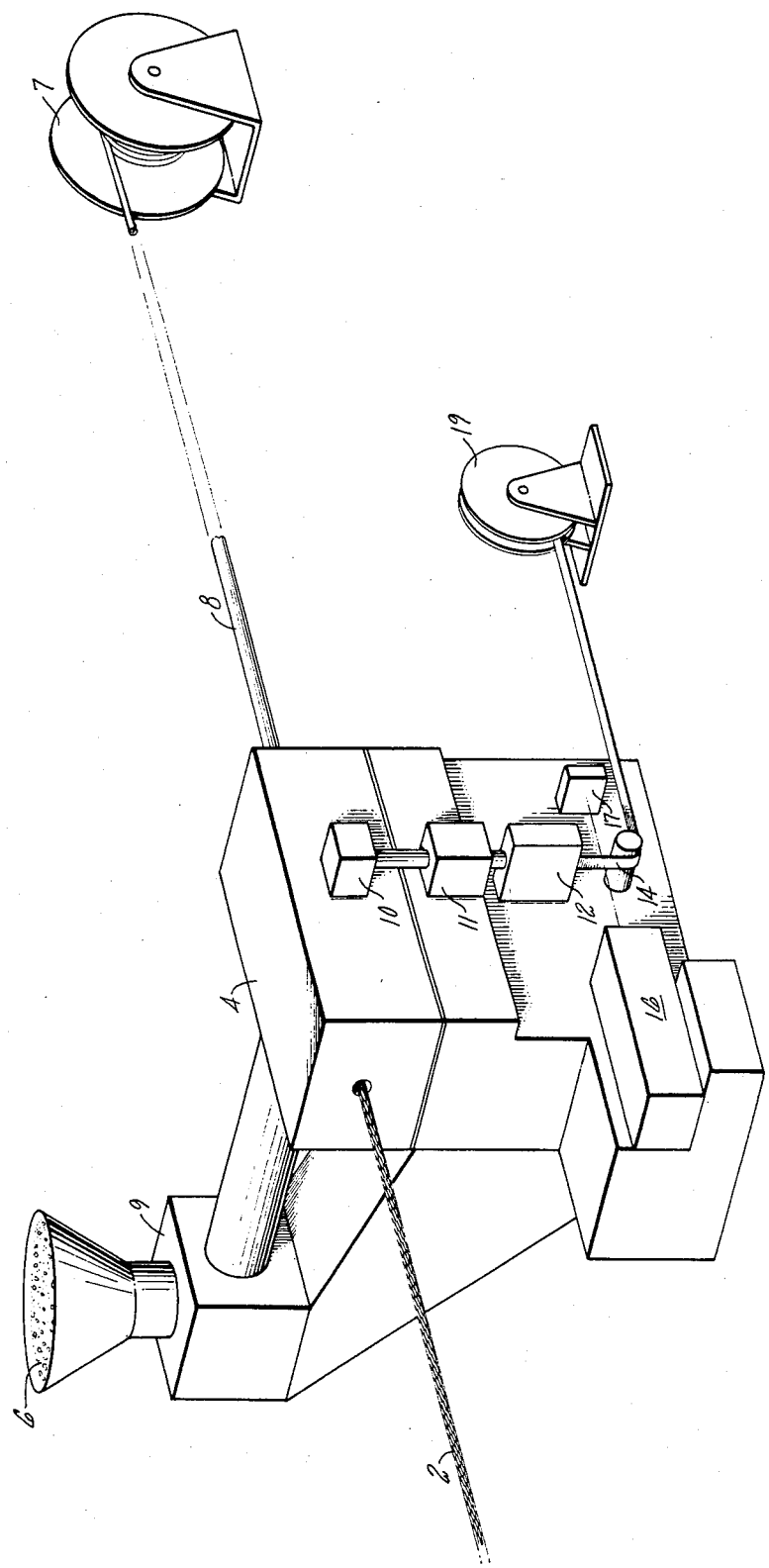

SYSTEM AND METHOD FOR IN-PROCESS DETECTION OF CONTAMINATION IN ELECTRICAL CONDUCTOR INSULATION

DESCRIPTION

TECHNICAL FIELD

The technical field to which this invention pertains is electrical conductor insulation and methods of inspecting the same. In particular, this invention is directed toward the electrical insulation of cables using polyethylene material.

BACKGROUND ART

Many electrical conductors are insulated with a layer of polyethylene material. Typically, this is done on a large scale by extruding the polyethylene onto the conductor as it passes through an extruder head. The speed at which the extrusion takes place may be in the order of a hundred feet per minute. This does not allow much time for in situ inspection of the resulting extruded insulation layer. Although the polyethylene insulation offers an excellent dielectric strength material, its effectiveness may be reduced by the presence of foreign objects such as dirt, carbon or other material with different dielectric strengths. The presence of these imperfections, which may be quite small, in the magnitude of 0.005 inch diameter or larger, causes localized electrical stresses within the insulation when voltage is applied to the cable. These resulting stresses create the well documented "treeing effect" in the insultion causing premature breakdown of the insulation and shorting of the cable life.

This problem of contamination has been of great concern to the electrical cable industry and a number of solutions have been proposed. One solution has been to have the material supplier inspect the polyethylene pellets prior to shipping to the cable manufacturer. However, their inspection techniques are subject to statistical error such that, for example, contaminants in the 0.004 inch range up to 0.010 inch range may be detected at a rate of only about 20 percent. This leaves a much larger amount of the contaminant behind in the raw polyethylene. In addition, such inspection techniques, even if 100 percent successful, are performed prior to shipping and extrusion onto the cable; while both the shipping and extrusion processes offer considerable opportunity for even further contamination.

A second technique which has been adopted by the Association of Edison Illuminating Companies (AEIC), is to inspect the insulation from the completed cable by physically excising a two-inch sample of completed cable for each ten thousand feet produced. These two-inch sections would then be sliced into wafers approximately 25 mils thick and physically examined under 15 power magnification for particulate contamination. This technique is also subject to much statistical error and may allow fairly large segments of contaminated cable to pass through undetected. In addition, this is a time consuming and labor intensive technique, which may be further affected by the proposed rules to increase the quantity of insulation inspected to 2 percent of the total insulating material prior to application to the cable.

The two-inch sampling technique mentioned above has a further drawback in that since this inspection takes place after the cable has been extruded, a great deal of money, time and resources has been expended on the production of this cable only to result in scraping the cable should a contaminated portion be found.

A further developement in contamination detection is an attempt to mechanize the previous inspection technique. In this technique, the insulation is inspected by directing a laser beam through the insulation and detecting the light scatter caused by the particle inclusions, thereby determining the amount of contamination present. A number of these systems have been designed for Electrical and Power Research Institute (EPRI) and are subjects of U.S. Pat. Nos. 4,208,126; 4,265,545 and are incorporated herein by reference. Unfortunately, these techniques require sophisticated laser tracking equipment and at the present are not cost effective.

Therefore, what is needed in the art is a cost effective method for detecting contaminants in the polyethylene insulation which would be representative of the insulating material in the as-applied condition and would allow for easy location of that contaminated portion of the cable simplifying removal of that portion.

DISCLOSURE OF THE INVENTION

The present invention discloses a method for inspecting optically transparent polyethylene insulation for contamination. The method comprises extruding a thin strip (tape) of the optically transparent, insulating polyethylene material simultaneously with the extrusion of the polyethylene insulation onto the cable. The resulting thin strip is then optically scanned for any contaminant which may be present. Additionally, since the strip is formed simultaneously with the extrusion of the insulation onto the cable, a given portion of the strip may be identified with a specific portion of the cable, allowing for simple and quick identification of a contaminated portion of cable insulation.

Other features and advantages will be apparent from the specification and claims and from the accompanying drawings which illustrate an embodiment of the invention.

BRIEF DESCRIPTION OF THE DRAWINGS

The FIGURE is a schematic of the extrusion process.

BEST MODE FOR CARRYING OUT THE INVENTION

The insulation which can be inspected by the present method is any optically transparent, polymeric material which will possess the requisite insulating properties required for a particular electrical cable application. The insulation should be free of any fillers or other materials which would not be optically transparent. The preferred materials are the conventional, polyethylene or cross-linked polyethylene insulating coatings. These may be high, low or medium density and may be cross-linked or noncross-linked. These materials would be extruded in a conventional manner. Typically, this means the pellitized polyethylene material is dumped into a hopper where it is transferred to the extruder and heated to a plastic state. The heated material is then extruded through the extruder head and about the conductor which is being drawn through the extruder head simultaneously. The insulation is then cooled forming the insulating layer. Subsequent cross-linking of the polyethylene insulating material, if necessary, may be done through vulcanization or irradiation in a conventional manner.

The cable may be any of the conventional electrical cables which are typically insulated using extrusion techniques. Many of these cables are designed to be used in medium or high voltage applications, i.e. above 5 kilovolts. These cables may be made from copper core, aluminum or the like and may be solid core or stranded.

Simultaneously, with the extrusion of the insulation onto the cable, is the extrusion of a thin tape of the insulation material through a side port or bleed port in the extruder head. Such a strip should be about 10 mils to about 25 mils thick and be about 1 inch to about 2 inches wide. However, it should be noted that under the proposed Association of Edison Illuminating Conpanies (AEIC) CS5-86 Specification for Thermoplastic and Cross-Linked Polyethylene Insulated Shielded Power Cables (9th Edition), inspection of the extruded insulated cable for a particular contaminant, should result in the inspection of 2 percent by weight of the total insulation placed on the cable. Therefore, the ribbon which is sampled should be designed to reflect about 2 percent sampling required by the AEIC.

Once the ribbon has been extruded, it is then optically scanned with any of the conventional optical scanners which are employed for inspecting polyethylene sheeting. The scanners comprise a laser beam energy surce which is passed through the ribbon of extruded insulation and by detecting, via a conventional optical detector, the loss of laser energy or dispersion of the laser beam due to contamination, the purity of the extruded insulation may be determined. These scanners are known and need not be described in detail here. Two such optical scanners which could be employed are described in U.S. Pat. Nos. 4,260,899 and 4,386,707 and are incorporated herein by reference.

In addition, the particular scanning device should be capable of detecting the defects present in the insulation which fall within the AEIC parameters. These parameters are such that the cable insulation shall contain no more than 15 contaminants ranging in size from 2-7 mils within 1 cubic inch of insulation. These contaminants may be carbon or dirt, other polymers PVC,EPR, etc., or cellulose such as paper or wood.

TABLE I

Allowable Contamination AEIC Specification C55-82

15 Contaminants
2-5 mils size
1 cubic inch

A typical system is schmatically depicted in the FIGURE. The conductor 2 is drawn into the primary extrusion head 4 wherein the insulating material 6 is heated 9 and is directed through a connector tube to the conductor where it coats the wire, resulting in an insulated cable 8 which is taken up on a take-up roll 7. Simultaneously to the extrusion of the insulation about the cable, a portion of the heated insulation 6 (typically 2 percent of the amount placed onto the cable) is forced out a bleed or sideport 10 in the primary extruder head 4, through an auxiliary heater 11 and through a ribbon die 12 which forms the material into a ribbon shape 14 of the desired thickness. The ribbon 14 is then inspected by the laser inspection tool 16 which directs a beam of light through the ribbon 14 which is detected by the detector 17 which can detect and record the impurities, if any, in the insulation. The tape may then be taken up on a take-up roll 19.

The particular extrusion head used to practice this invention may be conventional in nature, however, the extrusion process either in the head or in the hopper must have a means for diverting a certain amount of the insulating material to the ribbon forming means, i.e. a ribbon extruding die. Typically, a bleed port in the extruder head is used for this purpose. This directed material is then passed through a ribbon forming extruding die, where the insulating material is formed into a ribbon for inspection. Such ribbon dies are conventional, one such die is available from C. W. Brabender Instrument Incorporated, South Hackensack, N.J. and is listed as No. 05-55-005 and entitled A VERTICAL EXTRUDER. Such dies can form ribbons varying in size from about one to about six inches in width and up to about 60 mils in thickness. Other such ribbon dies may be available, allowing for varying extrusion dimensions if so desired.

The invention lies not in any uniqueness as to the individual component parts, but to the unique combination of these parts to solve this difficult problem which has been plaguing the electrical cable industry for some time. The process offers a number of advantages over those of the prior art. Initially, it offers a nondestructive testing capability for insulation, with a high confidence level. This is not available with the prior art methods of excising sections of the cable and examining them manually for contamination. Additionally, the method offers a form of inspection in real time, for the insulation as it is being applied to the cable. Therefore, any contamination which will result from within the heating or extrusion head apparatus will be detected prior to production of a large quantity of contaminated cable. A further advantage to the present system is that with the insulation in ribbon form, it is much simpler to examine. The laser inspection apparatus required for a ribbon is far less complicated than the inspection devices which have been proposed and employed to inspect the insulated cable itself. This means a cost saving for this system of up to ten times that of prior art.

It should be understood that the invention is not limited to the particular embodiments shown and described herein, but that various changes and modifications may be made without departing from the spirit and scope of this novel concept as defined by the following claims.

I claim:

1. A method for inspecting extrudable, optically transparent, polymeric electrical insulation for electrical cable comprising:

passing an electrical conductor through an extruder head;

introducing heated optically transparent polymeric insulating material into the extruder head, separating the heated polymeric material into two portions such that one portion is extruded onto the conductor and the other portion is formed into a ribbon;

passing the ribbon of optically transparent polymeric material out of the extruder head and in front of a laser energy source;

immediately passing a laser energy beam through the ribbon;

detecting the amount of radiation loss of the beam which passes through the ribbon;

classifying the insulation as acceptable or unacceptable based on the amount and size of laser radiation detected contaminants contained in the ribbon.

2. The method of claim 1 wherein a single ribbon comprises about 2 percent by weight of the total polymeric material directly related to footage of cable produced indicating the contamination level in the cable insulation.

3. The method of claim 1 wherein the optically transparent polymeric material is unfilled polyethylene or cross-linked polyethylene.

* * * * *